United States Patent [19]
Sanghvi et al.

[11] Patent Number: 5,851,555
[45] Date of Patent: Dec. 22, 1998

[54] CONTROLLED RELEASE DOSAGE FORMS CONTAINING WATER SOLUBLE DRUGS

[75] Inventors: Pradeepkumar P. Sanghvi, Herndon; Tushar K. Misra, Leesburg; David V. Prior, Ashburn, all of Va.

[73] Assignee: Fuisz Technologies Ltd., Chantilly, Va.

[21] Appl. No.: 914,339

[22] Filed: Aug. 15, 1997

[51] Int. Cl.⁶ .............................. A61K 9/20; A61K 9/22; A61K 9/26
[52] U.S. Cl. .......................... 424/464; 424/465; 424/468; 424/470
[58] Field of Search ..................................... 424/476, 489, 424/469, 468, 464, 470, 484, 465

[56] References Cited

U.S. PATENT DOCUMENTS 5,334,393  8/1994  Bougaret et al. ........................ 424/469

OTHER PUBLICATIONS

Bougaret et al., *Chemical Abstracts,* vol. 116, #221593, 1991.

*Primary Examiner*—Thurman K. Page
*Assistant Examiner*—Sharon Howard
*Attorney, Agent, or Firm*—Sandra M. Nolan

[57] ABSTRACT

Controlled release dosage units containing water soluble active agents can be made using an active agent, an optional inert carrier, a cellulosic polymer and a lipophilic ingredient.

17 Claims, No Drawings

CONTROLLED RELEASE DOSAGE FORMS CONTAINING WATER SOLUBLE DRUGS

BACKGROUND OF THE INVENTION

Isosorbide 5-mononitrate is one of a group of active agents whose therapeutic effects make it useful for the long-term treatment, or management, of disease states. Since these agents are used over long periods of time, the development of controlled release dosage forms containing them is desirable. However, many drugs of this type are water soluble or have other properties which make it difficult to prepare controlled release products containing them.

The processing difficulties encountered include sublimation—i.e., transition from a solid to a gas—under certain conditions encountered during processing; and poor controlled release properties due to the compounds' aqueous solubilities.

Isosorbide mononitrate is a useful model for the water soluble active agents which are beneficially administered in sustained release fashion. In addition, the compound is difficult to formulate due to sublimation and water solubility problems, as well as the fact that it generates static electric charges when it is processed alone in a dry form. For this reason, isosorbide 5-mononitrate is generally processed in the presence of an inert carrier.

Several attempts at producing controlled release pharmaceutical preparations containing isosorbide 5-mononitrate have been made. Among them are the technologies set out in the following patents and publications:

U.S. Pat. No. 4,812,316 shows the preparation of tablets containing isosorbide 5-mononitrate in which the drug is mixed with polyvinylpyrrolidone (PVP) to form a solid solution. This solution is then mixed with hydroxypropylmethylcellulose (HPMC) and other additives. The ratio of polymers (PVP plus HPMC) to drug is 1:5 to 5:1.

U.S. Pat. No. 4,389,393 deals with controlled release dosage forms which comprise less than 33% by weight of at least one hydroxypropylmethylcellulose polymer having a number average molecular weight of 50,000 or more.

U.S. Pat. No. 5,334,393 refers to a controlled release tablet containing isosorbide 5-mononitrate which is made by combining drug particles having four or more different sizes with a swellable hydrophilic polymer. The swellable polymers may be methyl- or propylcellulose polymers having viscosities of 0.1 to 100 Pa.s.

U.S. Pat. No. 5,453,283 discusses delayed release oral dosage forms containing isosorbide 5-mononitrate wherein the drug is melt-blended with a thermoplastic material (preferably polyvinylacetate) and a "structure former" (e.g., lactose).

There exists a need for compositions and processes for making orally-deliverable dosage forms containing water soluble drugs, which processes overcome the handling problems associated with these drugs and yield controlled release of the drug after ingestion. This invention addresses that need.

SUMMARY OF THE INVENTION

The invention deals with compositions and processes for making novel dosage forms and with the resultant dosage forms.

Applicants' compositions employ water soluble drugs, optionally blended with an inert carriers, which drugs or blends are combined with a cellulosic polymer and a lipophilic ingredient to yield controlled release dosage forms.

The making of dosage forms from these compositions will involve a solid dispersion, or hot melt blend, technique.

DETAILED DESCRIPTION

Unless otherwise stated, all parts and percentages stated are parts and percentages by weight based on total composition weight.

The invention deals with water soluble, difficultly processable, active agents which, when combined with optional carriers and other ingredients in solid dispersions, yield dosage forms giving controlled release of the drug upon oral administration. It deals with compositions and processes which are tailored to the particular handling and delivery requirements of those drugs.

For the drug isosorbide 5-mononitrate, the compound's propensity to generate static electricity, sublime, and dissolve readily are overcome via the use of an inert carrier, a cellulosic binder and a lipophilic ingredient which are combined in a solid dispersion.

For water soluble drugs with less stringent requirements, such as niacin, the drugs' handling problems are overcome by the use of the cellulosic polymer and the lipophilic ingredient in the solid dispersion.

Sublimation, which both isosorbide mononitrate and niacin exhibit, is one problem which use of the invention overcomes.

Generally, dosage units made using the invention give relatively slow rates of release, i.e., controlled release, over a period of about eight (8) to twenty four (24) hours.

THE COMPOSITIONS

The compositions of the invention contain, as essential ingredients, a water soluble active agent, an optional inert carrier, a cellulosic polymer and a lipophilic ingredient.

By "water soluble active agent" applicants mean compounds whose aqueous solubilities, in distilled water at 20° C., are 0.1 mg/mL or greater. Suitable active agents include: isosorbide 5-mononitrate, isosorbide dinitrate, niacin, diltiazem hydrochloride, pentoxyfylline, captopril and propranolol hydrochloride and the like, as well as mixtures and other pharmaceutically acceptable water soluble forms thereof.

Isosorbide 5-mononitrate, $C_6H_9NO_6$, is the major metabolite of the well-known antianginal compound isosorbide dinitrate.

Isosorbide dinitrate, $C_6H_8N_2O_8$, is an antianginal agent. Its aqueous solubiltiy is about 1.1 mg/ml.

Niacin or nicotinic acid, $C_6H_5NO_2$, is a well known vitamin and cholesterol lowering agent. One gram of the compound dissolves in 60 mL of water.

Diltiazem hydrochloride, $C_{22}H_{26}N_2O_4S.HCl$, is freely soluble in water. It is used to treat angina, hypertension and arrhythmia.

Pentoxyfylline, $C_{13}H_{18}N_4O_3$, is a vasodilator. Its aqueous solubility is 77 mg/mL at 25° C.

Captopril, $C_9H_{15}NO_3S$, is freely soluble in water. It is an antihypertensive agent.

Propranolol hydrochloride, $C_{16}H_{21}NO_2.HCl$, is water soluble. It is used to treat hypertension, angina and arrhythmia.

When special handling considerations require it, the active agent and an inert carrier are premixed separately, generally as a dry preblend. The inert carrier used is typically a non-reactive excipient. Suitable carriers include one or more of silica, silicates, cellulose and saccharides, such as lactose. Lactose is very useful.

The ratio of active agent to carrier should be about 4:1 to 3:2. Ratios of 4:1 to 7:3 are typical.

The cellulosic polymer is a high molecular weight hydroxypropylmethylcellulose (HPMC) polymer. This HPMC polymer has an average molecular weight of about 25,000 to about 300,000, with those having molecular weights of about 120,000 to about 130,000 and viscosities in 2% aqueous solutions of about 100 to about 100,00 mPa.s at 20° C. being very effective. Useful HPMC polymers include that sold under the trade name METHOCEL K15M (Dow Chemical), a solid having an average molecular weight of about 124,000 and a viscosity of about 15,000 mPa.s in 2% aqueous solutions at 20° C.

The lipophilic ingredient is employed in compositions to be combined using solid dispersion, or melt blending, techniques. The ingredient used is generally a fatty acid ester. All or part of the ester component may be replaced by one or more of wax, fat or cetyl alcohol ingredients. An effective lipophilic ester is glyceryl behenate, sold as COMPITROL 888 ATO (Gattefosse S.A.).

Various additives which are commonly used in tablet formulations can be included. Among these are fillers, auxiliary binders, flow control agents, lubricants, flavorants, fragrances, colorants and the like.

One typical flow control agent is colloidal silica. Such silicas, or silicon dioxides, are conventional glidants in tablet compositions. They have surface areas ranging from about $50m^2/g$ to about $400m^2/g$. CAB-O-SIL (Cabot) is useful.

Another typical additive is a microcrystalline cellulose stiffening agent. AVICEL PH101 (FMC) is particularly useful.

The compositions will generally contain one or more lubricants. Suitable lubricants include fatty acid salts, talc, stearic acid and magnesium stearate. Magnesium stearate is highly effective.

The colorant used can be any of a wide variety used in pharmaceutical preparations. Pigments, dyes and lakes are used in conventional amounts. Iron oxide is a useful pigment.

Flavorants, e.g., sweeteners, and fragrances can also be added.

Suitable quantities of these and other additives will be determined by their functions in the formulation as well as the overall character of the final dosage form. Generally, amounts of such excipients will range from about 0% to about 50%.

The following table sets out broad and preferred ranges for each of the ingredients typically found in applicants' formulations. Other ingredients can be used.

| INGREDIENT | BROAD RANGE (pts) | PREFERRED RANGE (pts) |
|---|---|---|
| ACTIVE AGENT | 15–25 | 18–20 |
| INERT CARRIER | 0–15 | 4–9 |
| CELLULOSIC POLYMER | 25–45 | 30–38 |
| LIPOPHILIC INGREDIENT | 0.1–35 | 30–35 |
| MICROCRYSTALLINE CELLULOSE | 0.5–45 | 1–40 |
| COLLOIDAL SILICA | 0.1–5 | 0.5–2 |
| LUBRICANT | 0.1–5 | 0.5–2 |

MIXING AND COMPRESSING PROCEDURES

The ingredients in applicants' compositions are combined and processed using solid dispersion, or melt blending, procedures.

The description set out below is general in nature. Changes can be made to tailor this procedure to particular needs.

The following examples show optional embodiments employing dry-mixed pre-blends of an active agent with lactose or another inert carrier. The same techniques can be employed using active agents without inert carriers.

The inventive process typically uses the following steps:

(1) mixing the active agent, or active agent/carrier pre-blend, with lipophilic ingredient, cellulosic polymer, and a portion of the excipients;

(2) heating the mixture from step (1) with further mixing to melt the lipophilic ingredients and form aggregates;

(3) granulating the aggregates from step (2);

(4) mixing the granulate of step (3) with the remaining excipient portion; and (5) compressing into tablets.

Compression is carried out using about 12 to about 24 killonewton (kN) at room temperature on a rotary tablet press.

The tablets have hardnesses of 30 N to 200 N, and preferably 50 N to 90 N.

While oral dosage forms, i.e., tablets, are described here, dosage forms for other routes of administration can also be made using the invention.

EXAMPLES

The following example(s) illustrate the compositions and procedures used in connection with the invention:

EXAMPLE I

The following ingredients were mixed in a Patterson-Kelley V-core blender for about 30 minutes (total time):

| INGREDIENT | PTS |
|---|---|
| ISOSORBIDE 5-MONONITRATE/LACTOSE (4:1 PRE-BLEND) | 30.6 |
| COMPRITOL 888 ATO | 40.0 |
| METHOCEL K15M | 25.0 |
| AVICEL PH101 | 2.37 |
| CAB-O-SIL | 1.0 |
| MAGNESIUM STEARATE | 1.0 |

The mixture was heated at 70° C. to 90° C. for about three hours with stirring at one-hour intervals. This blend was mixed and chopped in a high shear mixer for about six minutes to yield a granulate. The granulate was cooled for 1 to 24 hours and milled to achieve a particle size of less than 850 microns.

The granulate was combined with additional components as follows:

| COMPONENT | PTS |
|---|---|
| GRANULATE | 80.0 |
| METHOCEL K15M | 19.0 |
| CAB-O-SIL | 0.5 |
| MAGNESIUM STEARATE | 0.5 |

The granulate, METHOCEL and CAB-O-SIL were mixed in a Patterson-Kelley V-core blender for a total of about 30 minutes. The magnesium stearate was added and the blender was run for about five minutes to yield the final blend.

This blend was tableted in a rotary tablet press at 40 Hz. The tablets weighed 315 mg and had 70 N hardness.

Bioassay testing showed that tablets using the invention has a $T_{max}$ value of 3.8 hours. This is comparable to the 4.0 hour $T_{max}$ value of IMDUR, a commercial product.

$T_{max}$ is an in vivo measure of the time until the maximum blood plasma level ($C_{max}$) of an active ingredient is attained. The $T_{max}$ studies involved the following steps: 60 mg tablets were administered orally to volunteers. At hourly intervals, blood samples are taken and the concentration of the active agent in plasma is measured. After plots are made of concentration vs. time, $C_{max}$ and $T_{max}$ values are assigned.

Dissolution studies compared the properties of solid dispersion tablets to IMDUR tablets. IMDUR (Key Pharmaceuticals) is a commercially available extended release formulation containing isosorbide mononitrate. Its ingredients are listed in the 1997 Physician's Desk Reference at page 1362.

Tests were run on 60 mg tablets of the solid dispersion product and IMDUR using standard dissolution techniques, in a U.S.P. Apparatus I, at 100 rpm, with 900 mL distilled water at 37° C.

A comparison of the dissolution properties of solid dispersion tablets to those of IMDUR tablets is shown below.

| | Percent Dissolved | |
|---|---|---|
| Time (hr) | Solid Dispersion Tablet | IMDUR Tablet |
| 1 | 25.6 | 36.2 |
| 2 | 37.6 | 50.5 |
| 4 | 54.8 | 70.0 |
| 6 | 68.0 | 82.7 |
| 8 | 78.3 | 90.8 |
| 10 | 86.4 | 96.2 |

Tablets made in accordance with the invention dissolve slightly more slowly than IMDUR tablets having the same concentration. Thus, the invention provides tablets which are useful in oral controlled release dosage forms.

Reasonable variations, such as those which would occur to a skilled artisan, can be made herein without departing from the scope of the invention.

We claim:

1. Compositions suitable for making controlled release dosage forms consisting essentially of
   about 5 to about 40 parts of a water soluble active agent;
   about 0 to about 15 parts of an inert carrier;
   about 5 to about 45 parts cellulosic polymer; and
   about 0.1 to about 45 parts lipophilic ingredient,
   wherein the lipophilic ingredient is at least one selected from the group consisting of: a fatty acid ester, a wax, a fat or cetyl alcohol.

2. The composition of claim 1 wherein the active agent is at least one selected from the group consisting of: isosorbide 5-mononitrate, isosorbide dinitrate, niacin, diltiazem hydrochloride, pentoxyfylline, captopril and propranolol hydrochloride.

3. The composition of claim 2 wherein the active agent is isosorbide 5-mononitrate and the inert carrier is lactose.

4. The composition of claim 3 wherein the polymer is a hydroxypropylmethylcellulose polymer having an average molecular weight of about 25,000 to about 300,000.

5. The composition of claim 3 wherein the lipophilic ingredient is a fatty acid ester.

6. The composition of claim 5 wherein the ester is used in an amount of about 0.1 to about 45 parts.

7. A method of making a controlled release dosage unit comprising the steps of:

(1) mixing an active agent or active agent/carrier preblend with cellulosic polymer, lipophilic ingredient, fillers, and lubricant;

(2) melting, cooling, and milling the mixture of step (1) to yield a solid dispersion in granulate form;

(3) mixing the granulate of step (2) with additional amounts of cellulosic polymer, fillers, and lubricant; and (4) compressing the mixture of step (3) into a dosage unit, wherein the lipophilic ingredient is at least one selected from the group consisting of: a fatty acid ester, a wax, a fat or cetyl alcohol.

8. The method of claim 7 wherein the active agent comprises at least one agent selected from the group consisting of: isosorbide 5-mononitrate, isosorbide dinitrate, niacin, diltiazem hydrochloride, pentoxyfylline, captopril and propranolol hydrochloride.

9. The method of claim 8 wherein an active agent/carrier preblend containing isosorbide 5-mononitrate and lactose is used.

10. A dosage unit made via the method of claim 8.

11. The dosage unit made via the method of claim 9.

12. A controlled release dosage unit produced from a composition comprising:
    about 5 to about 40 parts of a water soluble active agent;
    about 0 to about 15 parts of an inert carrier;
    about 5 to about 45 parts cellulosic polymer; and
    about 0.1 to about 45 parts lipophilic ingredient,
    wherein the lipophilic ingredient is at least one selected from the group consisting of: a fatty acid ester, a wax, a fat or cetyl alcohol.

13. The dosage unit of claim 10 wherein the active agent is at least one selected from the group consisting of: isosorbide 5-mononitrate, isosorbide dinitrate, niacin, diltiazem hydrochloride, pentoxyfylline, captopril and propranolol hydrochloride.

14. The dosage unit of claim 10 wherein the active agent is isosorbide 5-mononitrate and the inert carrier is lactose.

15. The composition of claim 1 wherein the active agent has an aqueous solubility of 0.1 mg/mL or greater.

16. The method of claim 7 wherein the active agent has an aqueous solubility of 0.1 mg/mL or greater.

17. The dosage unit of claim 12 wherein the active agent has an aqueous solubility of 0.1 mg/mL or greater.

* * * * *